US00PP30893P3

(12) United States Plant Patent
van Rosmalen

(10) Patent No.: US PP30,893 P3
(45) Date of Patent: Sep. 24, 2019

(54) ***HYDRANGEA* PLANT NAMED 'HORE0007'**

(50) Latin Name: *Hydrangea macrophylla*
Varietal Denomination: HORE0007

(71) Applicant: Nick van Rosmalen, Velp (NL)

(72) Inventor: Nick van Rosmalen, Velp (NL)

( * ) Notice: Subject to any disclaimer, the term of this patent is extended or adjusted under 35 U.S.C. 154(b) by 0 days.

(21) Appl. No.: 16/350,099

(22) Filed: Sep. 25, 2018

(65) Prior Publication Data

US 2019/0104665 P1 Apr. 4, 2019

Related U.S. Application Data

(60) Provisional application No. 62/606,622, filed on Sep. 29, 2017.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 6/48
See application file for complete search history.

*Primary Examiner* — Annette H Para
(74) *Attorney, Agent, or Firm* — C. A. Whealy

(57) ABSTRACT

A new and distinct cultivar of *Hydrangea* plant named 'HORE0007', characterized by its compact, upright and mounded plant habit; moderately vigorous to vigorous growth habit and moderate growth rate; freely branching habit with strong and sturdy stems; freely and uniformly flowering habit; mophead-type inflorescences with numerous green and red purple-colored sterile flowers that become more predominantly red purple with development; and good postproduction longevity.

3 Drawing Sheets

Botanical designation: *Hydrangea macrophylla.*
Cultivar denomination: 'HORE0007'.

BACKGROUND OF THE INVENTION

The present invention relates to a new and distinct cultivar of *Hydrangea* plant, botanically known as *Hydrangea macrophylla,* commercially referred to as a mophead-type *Hydrangea* and hereinafter referred to by the name 'HORE0007'.

The new *Hydrangea* plant is a product of a planned breeding program conducted by the Inventor in Velp and Reeuwijk, The Netherlands. The objective of the breeding program was to create new compact and freely-branching *Hydrangea* plants with strong sturdy stems, large inflorescences with numerous attractive sterile flowers and good postproduction longevity.

The new *Hydrangea* plant originated from a cross-pollination made by the Inventor in July, 2011 in Velp, The Netherlands, of a proprietary selection of *Hydrangea macrophylla* identified as code number 12-00-74, not patented, as the female, or seed, parent with a proprietary selection of *Hydrangea macrophylla* identified as code number 12-00-03, not patented, as the male, or pollen, parent. The new *Hydrangea* plant was discovered and selected by the Inventor as a single flowering plant from within the progeny of the stated cross-pollination in a controlled greenhouse environment in Reeuwijk, The Netherlands in June, 2013.

Asexual reproduction of the new *Hydrangea* plant by vegetative tip cuttings in a controlled environment in Reeuwijk, The Netherlands since August, 2015 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HORE0007'. These characteristics in combination distinguish 'HORE0007' as a new and distinct *Hydrangea* plant:

1. Compact, upright and mounded plant habit.
2. Moderately vigorous to vigorous growth habit and moderate growth rate.
3. Freely branching habit with strong and sturdy stems.
4. Freely and uniformly flowering habit.
5. Mophead-type inflorescences with numerous green and red purple-colored sterile flowers that become more predominantly red purple with development.
6. Good postproduction longevity.

Plants of the new *Hydrangea* can be compared to plants of the female parent selection. Plants of the new *Hydrangea* differ primarily from plants of the female parent selection in the following characteristics:

1. Plants of the new *Hydrangea* are more freely flowering than plants of the female parent selection.
2. Plants of the new *Hydrangea* have longer postproduction longevity than plants of the female parent selection.

Plants of the new *Hydrangea* can be compared to plants of the male parent selection. Plants of the new *Hydrangea* differ primarily from plants of the male parent selection in the following characteristics:

1. Plants of the new *Hydrangea* are more freely flowering than plants of the male parent selection.

2. Inflorescences of plants of the new *Hydrangea* are more globular than and not as flat-top as inflorescences of plants of the male parent selection.
3. Sterile flowers of plants of the new *Hydrangea* are darker in color than sterile flowers of plants of the male parent selection.

Plants of the new *Hydrangea* can be compared to plants of the *Hydrangea macrophylla* 'Schloss Wackerbarth', not patented. In side-by-side comparisons, plants of the new *Hydrangea* differ primarily from plants of 'Schloss Wackerbarth' in the following characteristics:

1. Plants of the new *Hydrangea* have stronger stems than plants of 'Schloss Wackerbarth'.
2. Inflorescences of plants of the new *Hydrangea* are more uniformly rounded than and not as uneven as inflorescences of plants of 'Schloss Wackerbarth'.
3. Plants of the new *Hydrangea* have longer postproduction longevity than plants of 'Schloss Wackerbarth'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HORE0007' during an early stage of development.

The photograph at the top of the second sheet is a close-up view of a typical developing inflorescence of 'HORE0007'.

The photograph at the bottom of the second sheet is a close-up view of a typical leaf of 'HORE0007'.

The photograph on the third sheet is a side perspective view of a typical flowering plant of 'HORE0007' at a stage of full development.

DETAILED BOTANICAL DESCRIPTION

Plants used in the aforementioned photographs and in the following description were grown during the summer in 13-cm containers in a glass-covered greenhouse in Reeuwijk, The Netherlands and under cultural practices typical of commercial *Hydrangea* production. During the production of the plants, day temperatures ranged from about 20° C. to 35° C. and night temperatures ranged from about averaged 12° C. to 22° C. Plants of the new *Hydrangea* were two years old when the photographs and description were taken. Plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'HORE0007'.

Parentage:

*Female, or seed, parent.*—Proprietary selection of *Hydrangea macrophylla* identified as code number 12-00-74, not patented.

*Male, or pollen, parent.*—Proprietary selection of *Hydrangea macrophylla* identified as code number 12-00-03, not patented.

Propagation:

*Type cutting.*—By vegetative tip cuttings.

*Time to initiate roots, summer.*—About 16 days at temperatures about 20° C. to 30° C.

*Time to produce a rooted young plant, summer.*—About four months at temperatures about 20° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright and rounded plant habit; overall plant shape, broadly obovate; strong and sturdy stems; moderately vigorous to vigorous growth habit and moderate growth rate.

*Plant height.*—About 36.2 cm.

*Plant diameter or area of spread.*—About 42.3 cm.

Lateral branch description:

*Branching habit.*—Freely branching habit; when pinched, about eight lateral branches develop per plant.

*Length.*—About 22.6 cm.

*Diameter.*—About 6 mm.

*Internode length.*—About 4.2 cm.

*Texture.*—Smooth, glabrous; fully developed, woody.

*Aspect.*—Upright to about 40° from vertical.

*Strength.*—Strong, sturdy.

*Color.*—When developing: Close to 144B. Developed: Close to between 144A and 146B; at the nodes, tinged with close to N186C; when woody, close to 199C and 200C.

*Lenticels.*—Density: Medium. Size: About 1.5 mm by 0.75 mm. Color: Close to N186C.

Leaf description:

*Arrangement.*—Opposite, simple.

*Length.*—About 10.3 cm.

*Width.*—About 8.7 cm.

*Shape.*—Broadly ovate.

*Apex.*—Apiculate.

*Base.*—Truncate to broadly attenuate.

*Margin.*—Serrate.

*Texture, upper surface.*—Smooth to slightly rugose, glabrous.

*Texture, lower surface.*—Smooth to slightly rugose, sparse pubescence along veins.

*Venation pattern.*—Pinnate.

*Color.*—Developing leaves, upper surface: Close to NN137A. Developing leaves, lower surface: Close to between 146A and 147B. Fully developed leaves, upper surface: Slightly darker than between NN139A and 147A; venation, close to 145B. Fully developed leaves, lower surface: Close to 147B; venation, close to 145B.

*Petioles.*—Length: About 1.9 cm. Diameter: About 3 mm to 4 mm. Texture and luster, upper and lower surfaces: Smooth, glabrous; slightly glossy. Color, upper surface: Close to 145A. Color, lower surface: Close to 144B.

Flower description:

*Flower type and habit.*—Showy sterile flowers and small inconspicuous fertile flowers arranged on mophead-type terminal panicles; panicles rounded and flattened globular in shape; flowers face upright to outwardly depending on their position in the inflorescence.

*Fragrance.*—None detected.

*Natural flowering season.*—Early flowering habit, plants begin flowering about three months after planting; flowering begins in the late spring and is continuous until late summer in Northern Europe.

*Flower longevity.*—Fertile flowers last about five days on the plant, fertile flowers not persistent; sterile flowers last about six weeks on the plant, sterile flowers persistent.

*Quantity of flowers.*—Freely flowering habit; about 70 fertile flowers per panicle and about 120 sterile flowers per panicle.

*Panicle height.*—About 11.3 cm.

*Panicle diameter.*—About 16.8 cm.

*Fertile flower buds.*—Length: About 5 mm. Diameter: About 5 mm. Shape: Roughly globular. Color: Close to NN155A towards the base fading to close to N144D and at the base, close to 143A.

*Sterile flower buds.*—Length: About 7 mm. Diameter: About 1.1 cm. Shape: Broadly cup-shaped. Color: Close to 144B.

*Fertile flower diameter.*—About 7 mm.

*Fertile flower depth (height).*—About 6 mm.

*Sterile flower diameter.*—About 4.2 cm.

*Sterile flower depth (height).*—About 1.2 cm.

*Petals, fertile flowers.*—Quantity and arrangement: Five in a single whorl. Length: About 4 mm. Width: About 2.5 mm. Shape: Ovate, concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to 155A flushed with close to 76C. When opening and fully opened, lower surface: Close to between 155A and 158D.

*Petals, sterile flowers.*—Quantity and arrangement: Five in a single whorl. Length: About 3.5 mm. Width: About 1.75 mm. Shape: Ovate, concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to 75B. When opening and fully opened, lower surface: Close to 75A.

*Sepals, fertile flowers.*—Quantity and arrangement: Five in a single whorl. Length: About 2 mm. Width: About 1.75 mm. Shape: Broadly ovate. Apex: Acute. Base: Broadly cuneate. Margin: Entire. Texture and luster, upper and lower surfaces: Smooth, glabrous; slightly glossy. Color: When opening, upper and lower surfaces: Close to 143A fading towards the base to close to N144D. Fully opened, upper and lower surfaces: Close to 143B fading towards the base to close to 145B.

*Sepals, sterile flowers.*—Quantity and arrangement: Four or occasionally five in a single whorl. Length: About 2.2 cm. Width: About 2.2 cm. Shape: Broadly ovate. Apex: Broadly and bluntly acute. Base: Broadly cuneate. Margin: Entire. Texture and luster, upper and lower surfaces: Smooth, glabrous; matte. Color: When opening, upper surface: Close to 143A heavily flushed and marbled with close to 61C. When opening, lower surface: Close to 148D heavily flushed and marbled with close to 62B to 62C. Fully opened, upper surface: Close to 143A, N144A and N144B heavily flushed and marbled with close to between 61B to 63A; color becoming predominantly more red purple with development. Fully opened, lower surface: Close to 138B heavily flushed and marbled with close to 62B to 62C; color becoming predominantly more red purple with development.

*Pedicels, fertile flowers.*—Length: About 3 mm. Diameter: About 1 mm. Strength: Moderately strong. Aspect: About 10° from vertical. Texture and luster: Sparsely pubescent; matte. Color: Close to 145D.

*Pedicels, sterile flowers.*—Length: About 3.3 cm. Diameter: About 1.5 mm. Strength: Moderately strong. Aspect: About 35° from branch axis. Texture and luster: Pubescent; matte. Color: Close to 70C fading proximally to close to 157A.

*Reproductive organs, fertile flowers.*—Stamens: Quantity per flower: About ten. Filament length: About 1.5 mm. Filament color: Close to NN155D. Anther length: About 0.75 mm. Anther shape: Broadly oblong. Anther color: Close to 155A. Pollen amount: Moderate. Pollen color: Close to 158D. Pistils: Pistil quantity per flower: Three. Pistil length: About 1.75 mm. Stigma shape: Club-shaped. Stigma color: Close to 145D. Style length: About 0.75 mm. Style color: Close to 145D. Ovary color: Close to 145D.

*Reproductive organs, sterile flowers.*—Stamens: Quantity per flower: About ten. Filament length: About 2 mm. Filament color: Close to NN155D. Anther length: About 1 mm. Anther shape: Broadly oblong. Anther color: Close to 155A. Pollen amount: Moderate. Pollen color: Close to 158D. Pistils: Pistil quantity per flower: Three. Pistil length: About 1 mm. Stigma shape: Club-shaped. Stigma color: Close to 157D. Style length: About 0.5 mm. Style color: Close to 157D. Ovary color: Close to 157D.

*Seeds.*—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HORE0007' as illustrated and described.

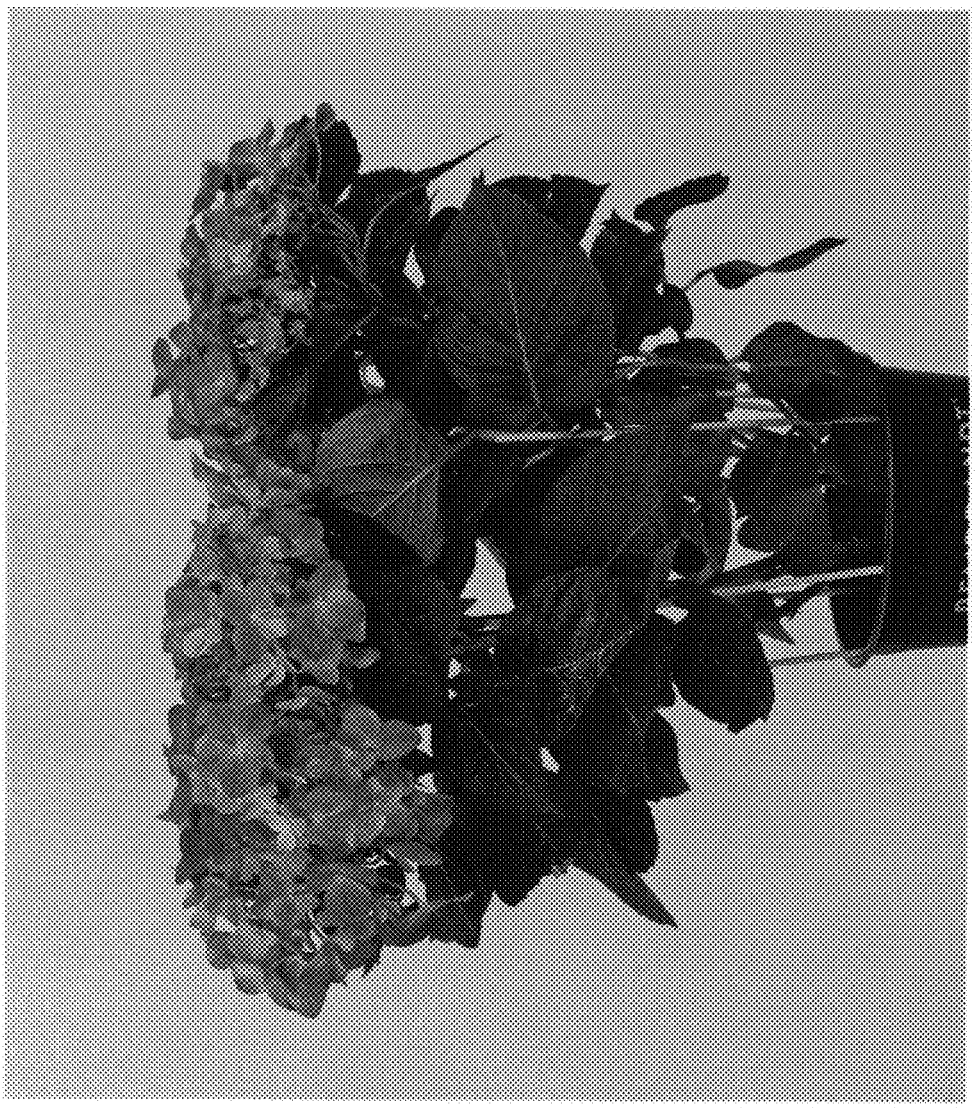

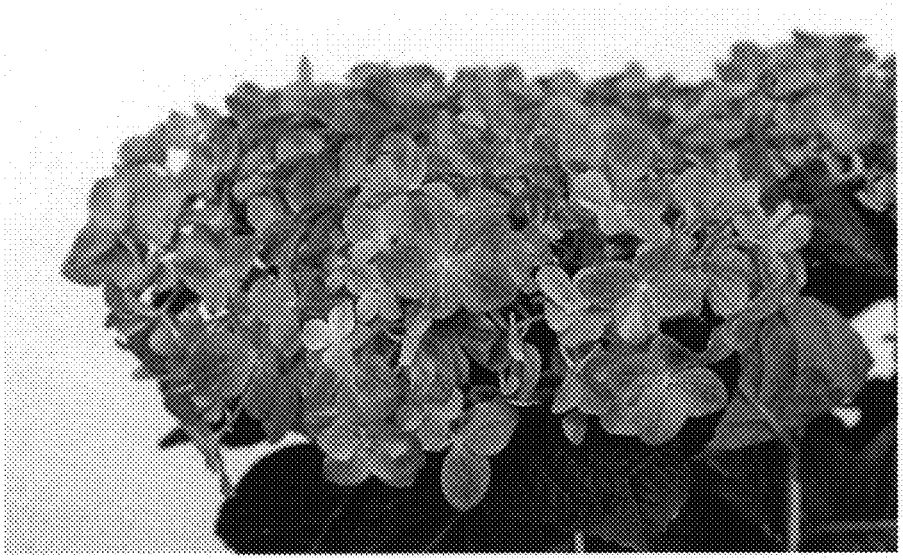
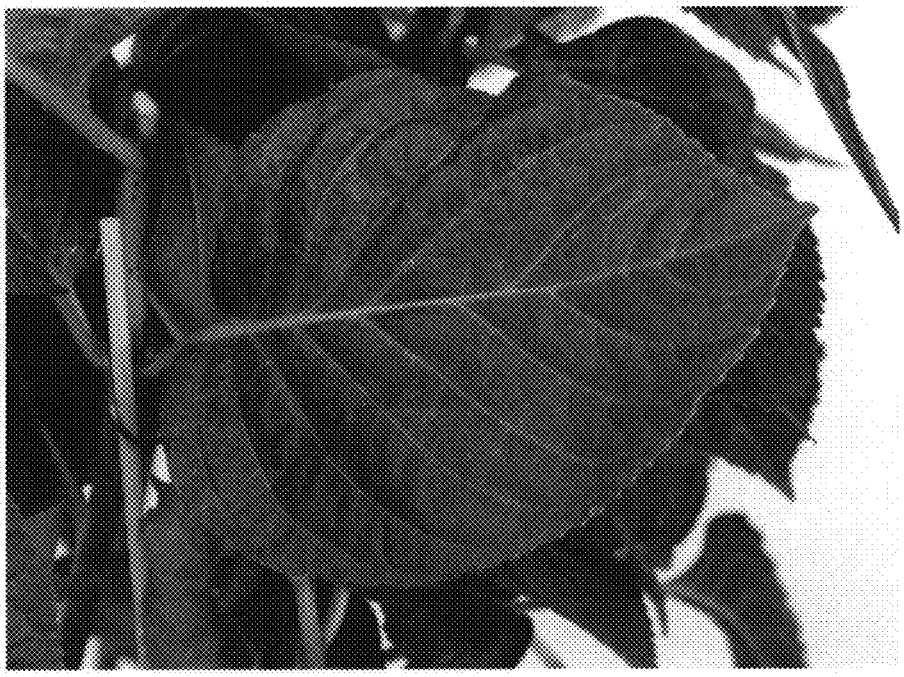

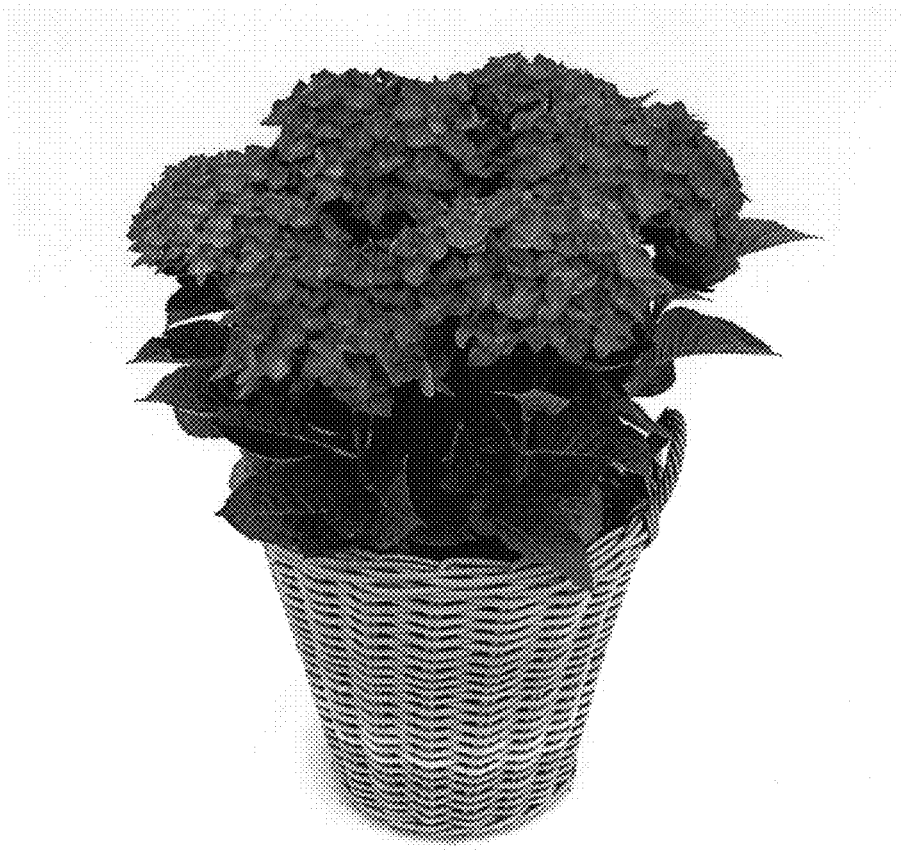

* * * * *